(12) United States Patent
Brault

(10) Patent No.: US 9,108,038 B2
(45) Date of Patent: Aug. 18, 2015

(54) MAGNETIC CONDUCTIVE DEVICE

(71) Applicant: Jean Brault, Cowansville (CA)

(72) Inventor: Jean Brault, Cowansville (CA)

(*) Notice: Subject to any disclaimer, the term of this patent is extended or adjusted under 35 U.S.C. 154(b) by 180 days.

(21) Appl. No.: 13/986,372

(22) Filed: Apr. 25, 2013

(65) Prior Publication Data

US 2013/0245359 A1    Sep. 19, 2013

Related U.S. Application Data

(63) Continuation-in-part of application No. 12/661,281, filed on Mar. 15, 2010, now abandoned.

(51) Int. Cl.
| | |
|---|---|
| *A61B 17/52* | (2006.01) |
| *A61N 2/00* | (2006.01) |
| *A61N 2/02* | (2006.01) |
| *A01G 7/04* | (2006.01) |
| *A61K 41/00* | (2006.01) |
| *A61M 37/00* | (2006.01) |

(52) U.S. Cl.
CPC .. *A61N 2/02* (2013.01); *A01G 7/04* (2013.01); *A61K 41/0004* (2013.01); *A61M 37/00* (2013.01)

(58) Field of Classification Search
CPC ........... A61N 2/00; A61N 2/02; A61N 2/002; A61N 1/445; A01G 7/04; A61K 41/0004; A61H 9/00; A61H 33/00; A61H 33/005; A61H 2009/0014; A61H 2009/0042; A61M 37/00; A61M 2037/0007; A61B 5/055
USPC ............ 600/9, 13, 10–12, 14–15, 544; 47/1.3
See application file for complete search history.

(56) References Cited

U.S. PATENT DOCUMENTS

| | | | | |
|---|---|---|---|---|
| 5,086,525 | A * | 2/1992 | Christopher | 4/498 |
| 5,741,317 | A * | 4/1998 | Ostrow | 607/85 |
| 6,427,479 | B1 * | 8/2002 | Komatsubara et al. | 62/503 |
| 7,187,969 | B2 | 3/2007 | Willis | |
| 2009/0049595 | A1 * | 2/2009 | Muller | 4/500 |

(Continued)

OTHER PUBLICATIONS

Hendee, W.R., Morgan, C.J., "Magnetic Resonance Imaging Part I—Physical Principles" [Medical Progress]. West J Med Oct. 1984; 141:491-500.*

(Continued)

*Primary Examiner* — Jacqueline Cheng
*Assistant Examiner* — Eileen Hyde

(57) ABSTRACT

A computerized electrical powered apparatus where one part is different types of housings with or without a cover. The apparatus produces magnetic field, for inducing water, in the housing (if a shower: inducing water, and water-vapor (mist) via a plumbing assembly). The housing uses: $CO_2$ liquid cooling to cool electrical circuit boards, electromagnet(s), nanotube(s), nanowire(s), that control: water, elements, nutrients, drugs, found in blood, living tissues, vegetation tissue(s) of any organism(s). In another aspect; an extractor capturing molecule(s) in steam derived from compounds, drugs, that converge with a superconductive wire transporting ionic compounds, molecular ions; rise out from hot water, $H_2O$-steam, and dry gases feed extractor, into a cooled catalyst pipe linking to a housing. The pipe with the wire inside, attach inside the housing, where the mixture disperses. A digital numerical image is captured on a computer monitor by rotating hydrogen molecules of water in the housing.

12 Claims, 8 Drawing Sheets

(56) References Cited

U.S. PATENT DOCUMENTS

2010/0155696 A1* 6/2010 Duan et al. ............... 257/14
2011/0077451 A1* 3/2011 Marchitto et al. ............ 600/13

OTHER PUBLICATIONS

F.H.Smirk, The effect of water drinking on the blood composition of human subjects in relation to diuresis. J of Physiol, May 23, 1933;vol. 78(2): p. 127-146 UCHMS,London England.

Pang Xiao Feng, Deng Bo, The changes of macroscopic features and structures of water under influence of magnetic field. Physica B 403 (2008)pp. 3571-3577. China.

Wangping Wu and Zhaofeng Chen, Growth mechanism of polycrystalline Ir coating by double glow plasma technology.Acta Metall.Sin.(Engl.Lett.)vol. 25 No. 6 pp. 469-479.(2012).China.

Fengyan Zhang,Robert Barrowcliff,Greg Stecker,Wei Pan, Deli Wang,Sheng-Teng Hsu.Synthesis of metallic Iridium oxide Nanowires via metal Ognanic Chemical VaporDeposition2005USA.

* cited by examiner

US 9,108,038 B2

MAGNETIC CONDUCTIVE DEVICE

This is a Continuation in part of, U.S. application Ser. No. 12/661,281 Dated: Mar. 15, 2010.

BACKGROUND OF THE INVENTION

1. Field of the Invention

The present invention relates to a magnetic field producing apparatus having a housing provided with or not a cover. The apparatus can have various types(s) of housings; and uses $CO_2$ liquid cooling. The housing provides magnetism induced water and to control: liquid content(s) in vegetation(s) tissues, blood content(s) circulating in living tissues; and for controlling small organism(s), cell(s). The invention further relates to molecule(s) captured in steam, derived from compounds, drugs; inside a dry gases (air, carbon dioxide $CO_2$, and oxygen $O_2$) hot water, $H_2O$-steam, feed extractor. The mixture is catalyzed, cooled, converges with a superconductive wire (capturing ionic compound(s), molecular ions) before entering the housing and dispersing as dry gases, water vapor (mist), laden with molecules, ionic compounds, molecular ions, for greater bioavailability by living tissues. A digital image is produced by repeated polarity rotation of hydrogen molecules, in living tissues.

2. Description of the Related Art

In the ongoing effort to better control administered drugs to a patient and following the process to reach the desired outcome during and after administration. Much has been aimed at controlling the quantities that are administered. Some examples of this are: Zero-order drug delivery using infusion pumps, time release drug patches, or the use of polymers such as described with U.S. Pat. No. 7,187,969 B2 entitled "ELECTROACTIVE PORE" John P. Willis, Mar. 6, 2007; and is included here as reference. However there has been less attempt at controlling the drugs once administered. Some exceptions to this, such as time release capsules, have some control after administration, in relation to time and quantity. However this does not address control over the drugs orientation once they have been administered, which leaves a blind spot as to the extent of their effectiveness. One example of this; is blood circulation, and the outcome this may have on the drugs distribution, where both benefits and repercussions may occur. For example: when the initial target was a specific organ or cell(s), however neighboring organs, or cells are effected and/or contaminated by the administered drugs, brought on by the process of blood circulation. Water is very prominent in blood circulation, throughout the body, as described in (The effect of water drinking on the blood composition of human subjects in relation to diuresis), F. H. Smirk J Physiol. VOL 78(2): 127-146) May 23, 1933 London ENGLAND. And included here as reference. Herein we further find that blood contains conductive properties electrolytes (minerals), ions, that are influenced by applied magnetic field.

In another study, the properties of water change when induced by magnetic field as described in, (The changes of macroscopic features and microscopic structures of water under influence of magnetic field), PANG XIAO FENG, DENG BO. Physica B 403 (2008) Pages 3571-3577. CHINA. And included here as reference.
On page 3576-3577, paragraph 4. CONCLUSION, we read:
"externally applied magnetic fields cause displacements and polarization of molecules and atoms, and result in changes of dipole moment in the transition and vibrational states of molecules."

Still further we read:
"magnetic field increases the refraction index, dielectric constant and electric conductivity of water."

The above facts prove not only is water, blood, and vegetation liquid controllable, using applied magnetic field. But, also find many occurring changes in water molecules, and other species of molecules that are affected as well; since we read:
"hydrophobicity of materials decrease after magnetization."

Given the small size of a living cell, and the intricate details within, such as the mitochondrial. Controlling such a living organism as a cell on the outside, requires nanosize equivalent tools, capable of maneuvering, without damaging. Even more so does this pose a problem when considering the inside of a cell. There is a much safer way using magnetism induced nanotubes, nanowires, sandwiched within diamagnetic materials, such as silicon, or graphene.

Purification, refinement, and extractions of compounds, for making drugs, and supplements, that can deliver the upmost bioavailability by living tissues is of prime importance in the health care industry, and for health care in general. The chemical breakdown of compounds, and energy exchanges, at the molecular scale, such as a catalyst reaction, is a natural occurring process, necessary for the absorption of nutrients by living tissues. One can think of photosynthesis as an example. A catalyst reaction is favored with the present invention. In another example: cloud formation, condensation, heat, convection, vapor, negative and positive charged ions (particles, dust), low temperatures, the growth of crystal(s) (snowflakes), are all found occurring in the upper Atmosphere. Likewise, the present invention uses heat, water, steam, along with pressure, dry gases (air, $CO_2$, and oxygen $O_2$) in the extraction process to free, and stimulate bioavailable molecule(s) from compounds and drugs found anywhere from solid to liquid state.

Similarly, cool conditions are favored by the present invention to optimized electrical conductivity; and in part for producing a catalyst reaction to form molecule(s) clusters, and ionic crystal(s). Cooling is also an important preventive measure that helps preserve molecules from fragmentation. Perishable organic compounds, perishable foods, are both good examples of molecule fragmentation.

Wire transport is nothing new, and is enabled over varied distances, such as phone, and cable lines, or nerve impulse in living tissues. Wire transport is used in part for extracting ionic compound(s), molecular ion(s) from compound(s), or drug(s) inside an extractor that is part of the present invention using; superconductive wire, given the dielectric constant, and hydrophobicity of materials decrease after magnetization, as described earlier.

Their is a need for a more in-depth alternative to digital imaging of the exterior, and interior of living tissues. It is possible to create a digital image from magnetism induced water, given the increased conductivity, and dielectric constant, described earlier.

SUMMARY OF THE INVENTION

In one aspect of the present invention, an apparatus for producing a magnetic field in a housing, forming a base member with a cover. However other types of housings are possible comprising: a shower, sauna, Jacuzzi, pool, aquarium, hydroponic container, green house, pipe plumbing assembly, water mixer chamber, steam water mixer chamber, bag, vial; and having a cover or not.

In an other aspect said apparatus provides: therapeutic treatment(s). Nutrients, drugs, in the form of molecule(s), ionic compound(s), and molecular ion(s), of high bioavailability for living tissues via an extractor and related part(s) that attach to a housing.

In one embodiment of the present invention using a magnetic field emitting housing (a cover and a base member) that has a very small cavity in the center of the base member for containing and controlling, the internal/external movements of small organism(s), cell(s), floating in magnetism induced water. The magnetic field provides exceptional maneuverability, and more so since a reduced hydrophobicity is brought on by the magnetized water.

Yet in another embodiment of the present invention; a magnetic field emitting housing that has carbon dioxide ($CO_2$) liquid coolant circulating in and out the inside structure walls of the housing. Thus cooling electronic(s) for greater conductivity, and higher para-magnetic, diamagnetic, and electromagnetic performances. Requiring lower magnetic frequencies; and therefore shorter time exposures under magnetic field to living tissues.

In other aspects the apparatus provides horticultural, agricultural, forestry, (application(s)) from a hydroponic container, or a shower producing magnetism induced ($H_2O$) derived steam, water, water vapor (mist), via a magnetic field induced plumbing assembly. Both of these housings can be attached to the extractor; to provide high end molecular, and ionic nutrients or chemical. For treating plant roots; via a hydroponic system. Or treating an entire plant, or other vegetation tissues using the shower system. A numerical digital image is produced, of an organism placed in a housing surrounded by magnetized induced water. By rotating the magnetic field; shifting the polarity within hydrogen molecules from north to south, in repeated manner. This sequence of events is further increased by pulsating the process; using the micro processors that control the electromagnets. And recording the events using a computer to process the information received from the vibrating hydrogen molecules, into numerical digital image on a computer monitor.

DETAILED DESCRIPTION OF THE INVENTION

The present invention is described with reference to the drawings.

A computerized apparatus that emits and controls magnetic field within a housing that enables to control liquids (water) therein via: North, South, East, West directions. And further control: nutrients, drugs, water and other elements found circulating in any organism(s) for example: human, cell, living tissues, blood, vegetation tissues, clone, animal, bacteria (via the internal cytoplasm), to name some. Said apparatus yet has various housing types; each providing unique treatments and applications.

Figure 1:
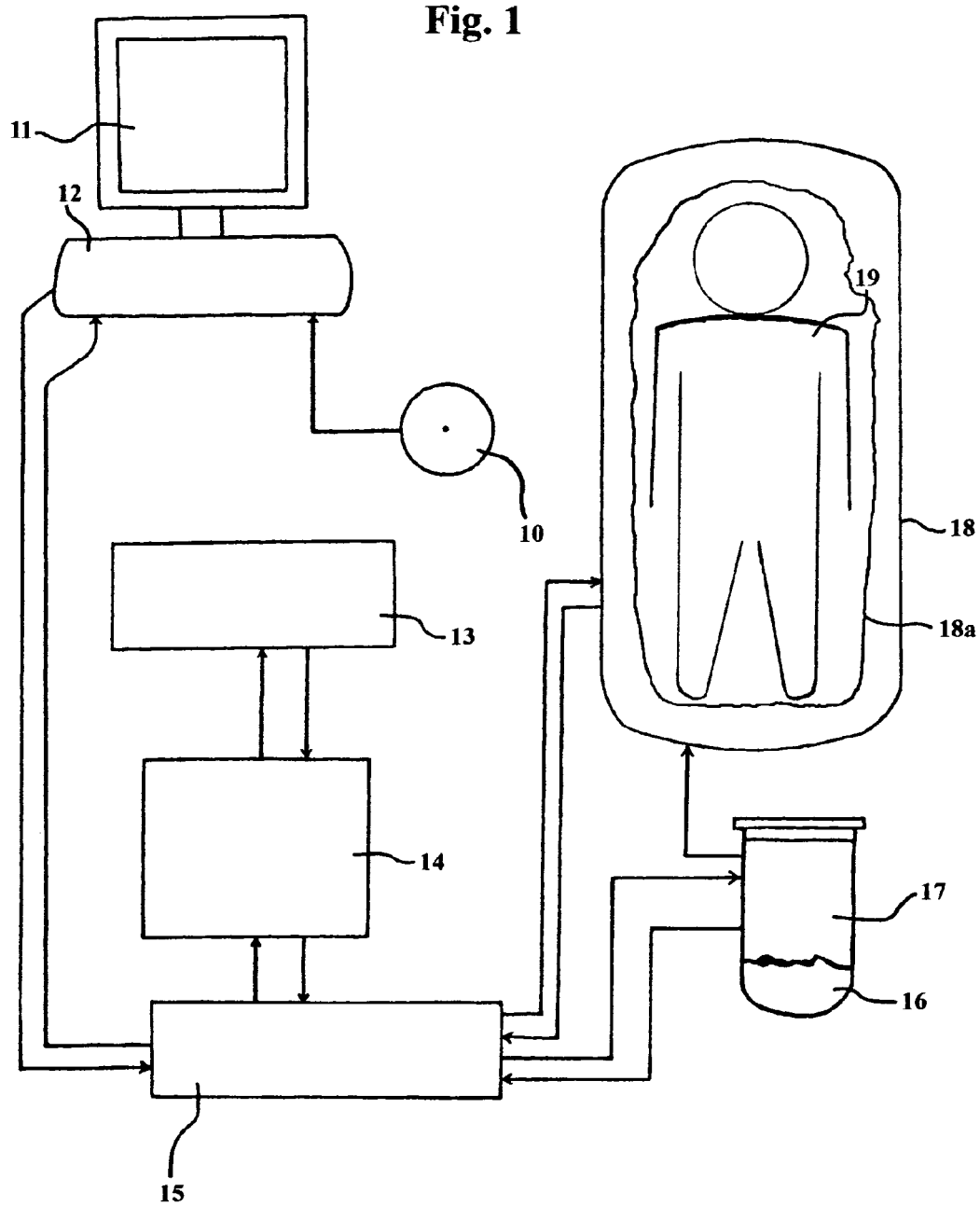
FIG. 1 is a block diagram showing an ensemble of a system having a magnetic conductive device, wherein, a base member of a housing (cover not shown herein), and an extractor according to embodiments of the present invention.

In an other equally important aspect of FIG. 1, an extractor 17 is described for providing the said housing (base member 18, and said cover mentioned above); with molecules, ionic compounds, molecular ions; all three deriving from compound(s), and/or drug(s) 16. However extractor 17 can provide the said molecules, ionic compounds, molecular ions for other types of housings, and applications that will be described with details further on.

Figure 6:
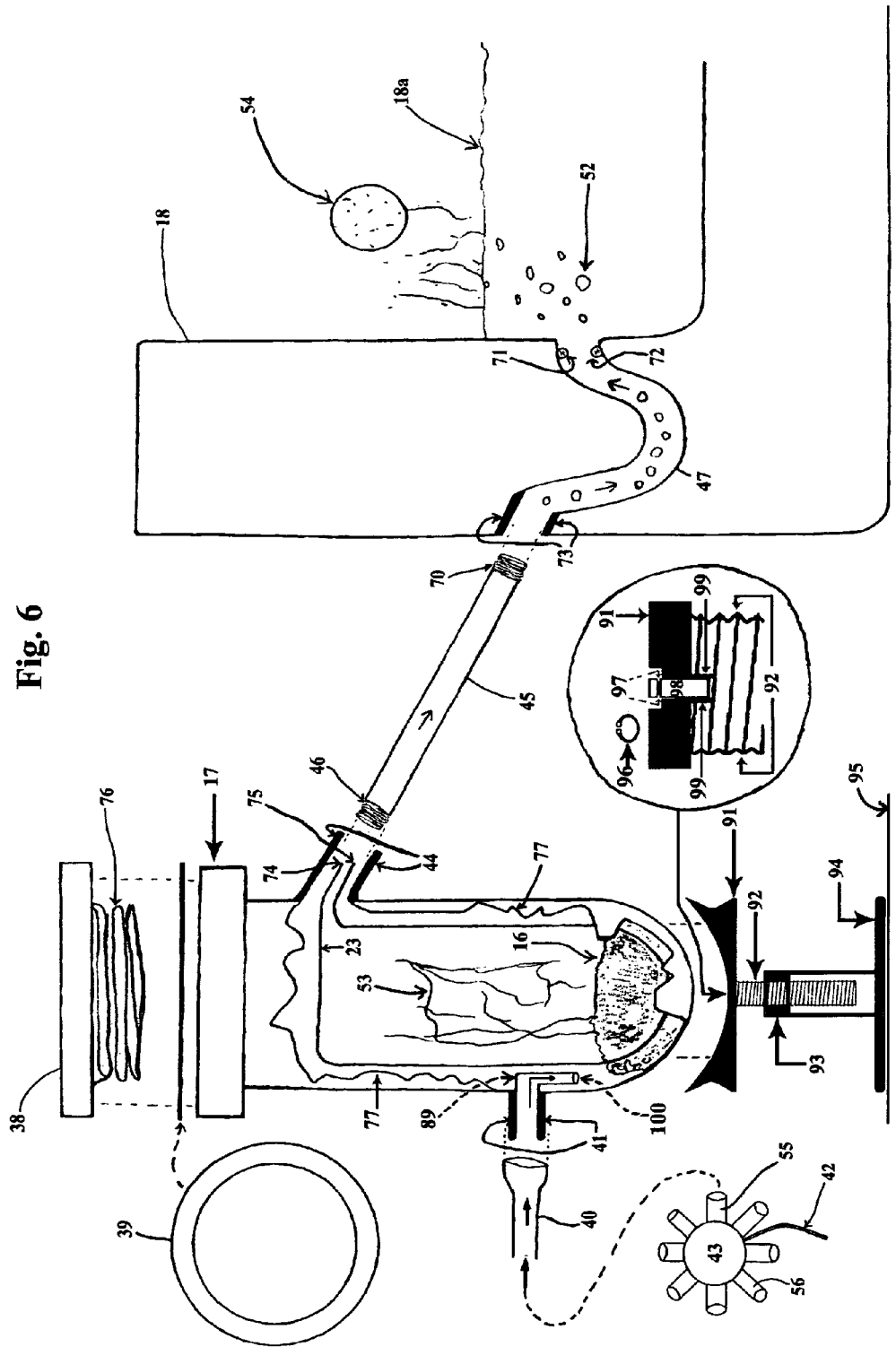
FIG. 6 Shows an exploded cross-sectional view of parts associated with an extractor that links with part of a housing (shown in a fractured view) for receiving a subject to (FIG. 1).
Figure 7:
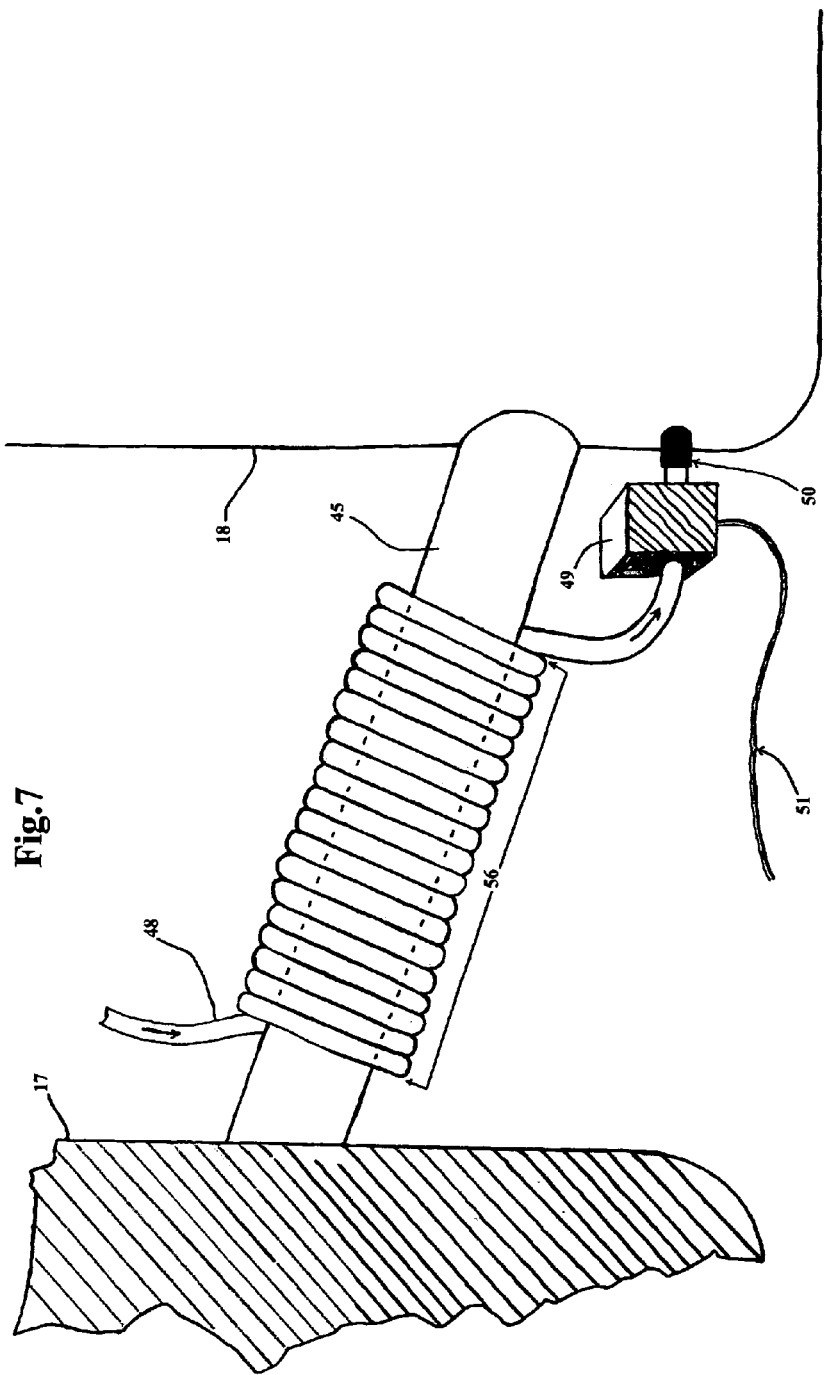
FIG. 7 is an exploded cross-sectional view of cryogenic tubing forming a tight coil around a pipe in the center thereof; linked on the left with a fractured view of an extractor; and to the right a fractured view of part of a housing, connected with a solenoid valve.
Figure 8:
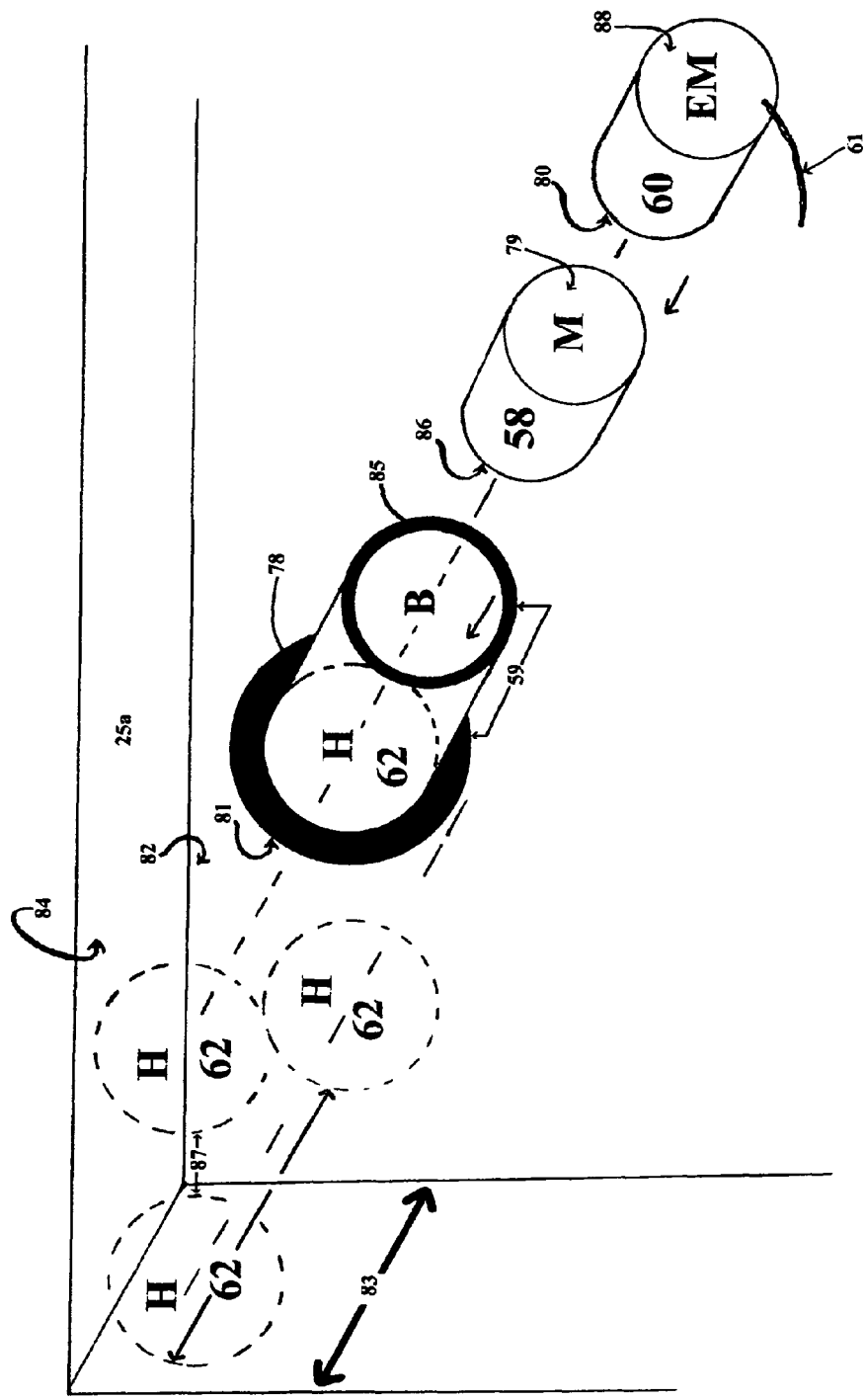
FIG. 8 Shows a cross-sectional view of parts: electromagnets, and para-magnets, associated with the interior paneling of a housing.

To provide a certain order and steps, and help the viewer save time and have a clear understanding; FIG. 6, FIG. 7, and most of FIG. 8; are explained thoroughly alongside of description to FIG. 1 and, FIG. 2. Capital letters found in FIG. 8, are for a quick reference to guide the viewer in the disposition and correlation of panel 25a (FIG. 8), with: holes 62 (FIG. 8)=H, flange bushing 59 (FIG. 8)=B, magnets 58 (FIG. 8)=M, and electromagnets 60 (FIG. 8)=EM.

FIG. 1, is a block diagram showing an ensemble of a system via several units, that forms part of an apparatus wherein a base member 18, is part of a housing for receiving a patient 19. Said housing to FIG. 1, further comprises a cover (not shown).

The housing to FIG. 1, emits a magnetic field inside (base member 18, and a cover). Said magnetic field is controlled via means that comprises:

software(s) 10, installed on a computer 12 having a computer monitor 11, and a processor configured to control a sequence unit 15; that controls an AC/DC power supply 13, where electric current is controlled via a current regulator 14. The sequence unit 15 may be coordinated via infra-red frequency transmitter/receiver. The applied magnetic field produced by the said housing (base member 18, and said cover) is achieved via several individual magnets; preferably electromagnets (solenoids). Herein the magnetic field is produced in the axial cylindrical bore of each coil containing a core preferably made of para-magnetic-ceramic compounds. Each electromagnets 60 (FIG. 8) are separately controllable, forming a layer inside the structure (wall) layer 25 (FIG. 2); wherein said electromagnets 60 (FIG. 8) are in contact with the back surface of interior surface wall panel 25a (FIG. 2) to both the base member 18 and cover of said housing. Electrical circuit boards having micro-processor(s) control each of the electromagnets 60 (FIG. 8). The electromagnets 60 (FIG. 8) are linked to the circuit boards via wires. It is important that each core contained within the said axil of the bore (hole) of each electromagnet 60 (FIG. 8) is of para-magnetic material composition; essentially (magnesium, molybdenum, lithium, and tantalum); to name some of the most common compounds. When the magnetic field is removed from electromagnets having a said para-magnetic core; the magnetic alignment is disrupted easily cut-off). Because they feature high thermal sensitivity unlike most electromagnets that use a permanent magnet core made of iron, or iron base compounds that are much less susceptible to thermal (temperature) variations. Therefore the response to said cut-off with the later (iron) is slower, and more so at very low magnetic fields then what the housing of the apparatus requires for adequate functioning. To further remedy this problem, and deliver even higher performance with electrical currant and magnetic field responses; the said housing is cooled using carbon dioxide ($CO_2$) liquid coolant as is described further on.

Figure 2:
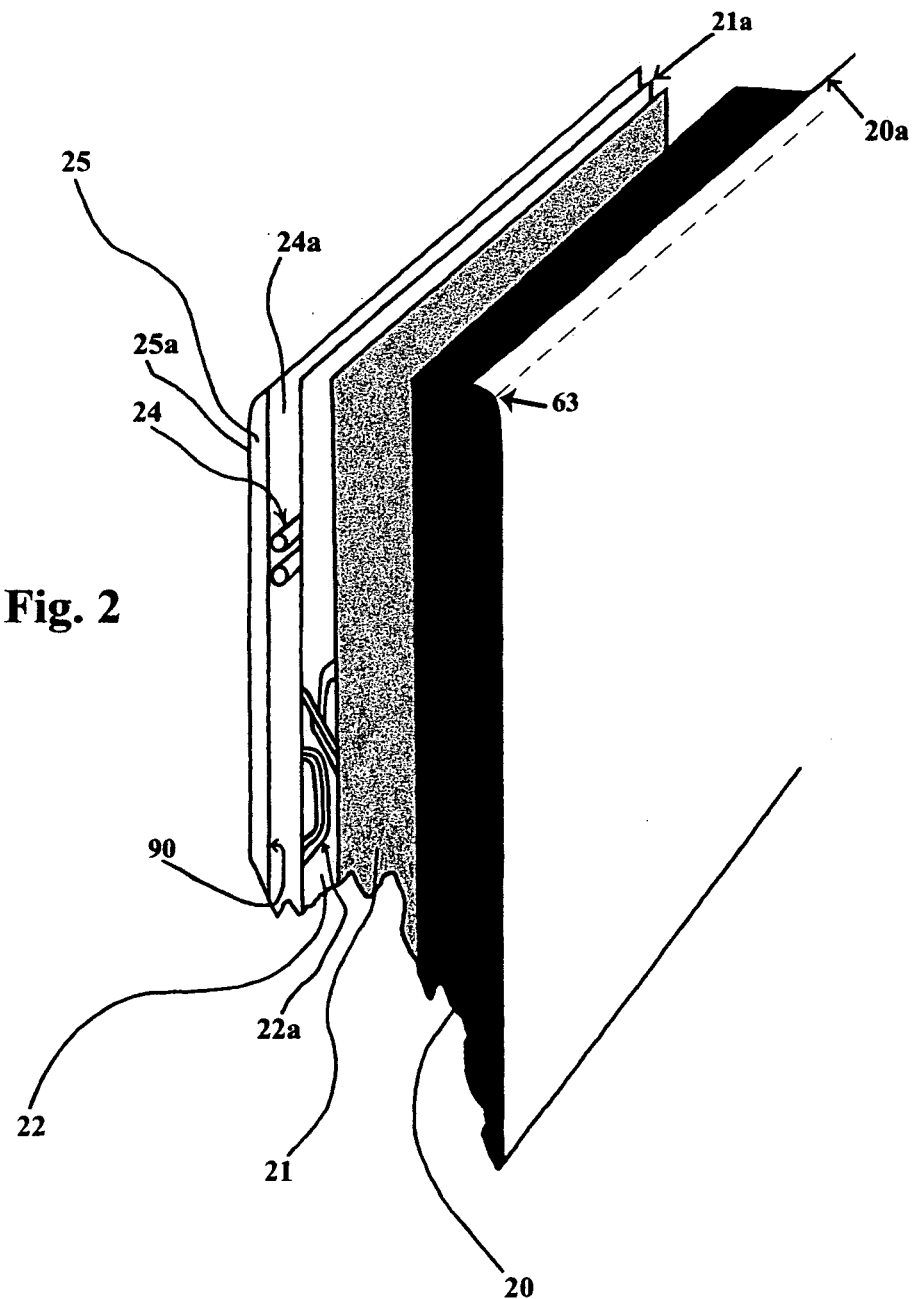
FIG. 2 is a diagram showing one detailed example of a structure of a magnetic conductive housing to (FIG. 1).

Each electromagnet 60 (FIG. 8) is separated one from another between 5 and 20 millimeters apart 87 (FIG. 8), on plastic paneling 25a that is coated with diamagnetic material(s), that preferably contains, carbon, such as graphene; forming a coating on the back surface of panel 25a (FIG. 2). The magnetic field strength developed from each of the electromagnets, is approximately between 0.5 Tesla and 2 Tesla. Each electromagnet 60 (FIG. 8) is in contact with an equal amount of para-magnets 58 (FIG. 8) that is explained in more detail in the housing structure of (FIG. 2).

This activates the magnetic field inside the housing; and in the process magnetism inducing the water 18a contained in the base member 18. Herein a patient 19 is placed into (at least partially surrounded/submerged) by the magnetism induced water 18a, for therapeutic treatments. The housing 18 controls water 18a via: North, South, East, West directions; and in turn water 18a controls: elements, water, nutrients, drugs, found in blood, living tissues, of the patient 19. However; the said apparatus provides other forms of treatments, and applications: horticultural, agricultural, forestry, application(s); that enables to control liquids, nutrient(s) circulating in vegetation tissues. To accommodate these and other treatments, and applications, said housing of the apparatus will be of a different type then the housing (base member 18 and cover) to FIG. 1. And therefore other housings comprising: a shower, sauna, Jacuzzi, pool, aquarium, hydroponic container, green house, bag, bowl, vial, water temperature control unit comprising: thermostatic mixing valve, hot, and cold water inlet(s), and/or outlet(s), plumbing valve, water mixers chamber(s), steam/cold water mixer(s); metal pipe plumbing assembly, plumbing assembly, Air/Gas diffuser; or any other shape of (housing), having a cover or not. A housing will have a drain according to type, and need of a housing.

A mixing container for liquids may be used, with a pump having a tube to replenish a housing for example: a hydroponic housing; before or during treatments, or therapy, submitted to a subject therein. Some examples: (water with magnetic beads, and fertilizer mixing for treating a plant roots), (Mineralized water).

A pump having a tube may be used to remove water, contaminated liquids from the housing for example: base member 18. The said tube from a pump may connect via the plumbing drain of a housing. Said liquids can then be decontaminated via a process liquid filter unit before sending it into a service drain.

Said cover for base member 18 is a removable cover, having 4 plastic handles (two handles per side that are located near the ends along the length of the cover). The cover is opened and closed manually; and can be removed completely via: lift off latch hinges that are convenient and preferable for maintenance, and known to the art. Up to 4 said hinges are located on one side along the length of the cover. A plexy glass window in the cover structure; sized to clearly see the neck and head of patient 19. Said window opens manually and is completely removed via lift off latch hinges. Air vents for evacuating heat and condensation via a vacuum (vacuum and vents described in FIG. 2). A water retaining o-ring seal found in a grove on the underside and along and near the cover's interior perimeter; that is aligned with a groove along the top perimeter of the base member 18.

In another embodiment of the present invention: an extractor 17, linking with the base member 18, (identified by an arrow line) and again in much detail showing the extractor 17 (FIG. 6) linking with base member 18 (FIG. 6)), and also in (FIG. 7). Said extractor 17 is shaped as a cylindrical housing made preferably of titanium, having diamagnetic material(s) a graphene coated, or gold plated interior; and containing a superconductive wire 23 (FIG. 6) forming a loop inside the extractor 17 (FIG. 6). The said loop part of superconductive wire 23 (FIG. 6) comes in contact with compound(s) and/or drug(s) 16 and 16 (FIG. 6) that are placed in the extractor 17, wherein said wire 23 (FIG. 6) serves for transporting ions containing a current charge, comprising: ionic compound(s), molecular ions (containing: electrons, protons, ions, neutrons, atoms). It is to be noted that other forms of molecule(s) for example: (carbon base molecules, organic molecules, neutral current charge molecules) not capture by said wire 23 (FIG. 6) are captured via steam; and is described further on. In the top of the extractor 17, herein is an opening that has female threads for receiving a removable cover 38 (FIG. 6) that has male threads 76 (FIG. 6). Said cover 38 (FIG. 38) is made preferably of titanium, having diamagnetic material(s) a graphene coated, or gold plated interior. A leak preventive flat ring 39 (FIG. 6) (a washer), made of rubber having a center hole fits between the cover 38 (FIG. 6) and the extractor cylindrical housing 17 (FIG. 6). The sequencing unit 15 controls via wiring 42 (FIG. 6) (wiring shown only in part) an electrical powered multi way solenoid valve 43 (FIG. 6) that is linked via a male outlet 55 (FIG. 6) to a plastic tube 40 (FIG. 6) that fits over said male outlet 55 (FIG. 6) and is secured by a plastic clamp (not shown). In turn the other end of plastic tube 40 (FIG. 6) then fits over a male inlet 41 (FIG. 6), located on the side of the extractor 17 (FIG. 6), (a damp holds the tube in place not shown). The plastic tube 40 (FIG. 6) supply's the extractor 17 (FIG. 6) with a mixture of dry gases preferably comprising: between 20% and 100% air coming from a medical air compressor. And no more then 0.020% (200 ppm) carbon dioxide ($CO_2$) (if needed, used as a buffer to oxygen ($O_2$)); and 60% or less oxygen ($O_2$). Said preferred air coming from said medical air compressor is used in part to add pressure (movement) and also to stimulate a Catalyst response inside the extractor 17 as it mixes with compounds and drugs 16. Dry gases (carbon dioxide ($CO_2$), and oxygen ($O_2$)) are used only by and if recommended by a health care professional how is providing the therapy to patient 19. Said medical air compressor in normal circumstances filters, monitors, and usually provides the best mixture of dry air (containing: carbon dioxide ($CO_2$), oxygen ($O_2$)); that can be furnished by laboratory, and hospital facilities via wall outlets. The said mixture (from tube 40 (FIG. 6) yet further comprising: between 1% and 50% hot water having a temperature range between 60° Celsius and boiling point, and between 25% and 50% steam (water-($H_2O$) derived type of steam), having a temperature range between 60° Celsius and boiling point. Boiling point is dependent on altitude and atmospheric pressure. Said multi way solenoid valve 43 (FIG. 6) serves to control flow pressure, and direction of flow. Said valve 43 (FIG. 6) links a plurality of plastic tubes (not shown) wherein each said tube fits over one of a plurality of the male inlets example 56 (FIG. 6), of valve 43 (FIG. 6). That is each male inlet example 56 (FIG. 6) separately carrying one dry gas: that is one for air, and one for carbon dioxide ($CO_2$), and one for oxygen. And also one male inlet example 56 (FIG. 6) separately carrying water, and one for steam (water-($H_2O$) derived type of steam). Each said male inlets of valve 43 (FIG. 6) is secured by a (plastic clamp not shown). Male inlet 55 (FIG. 6) is supplied with dry gases ($CO_2$) and oxygen via example: laboratory or Hospital, facility wall outlet; or via pressurized storage tanks. Water is provided via tap, ($H_2O$)-steam via a steam cold water mixer (known to the art).

A fractured view inside the extractor 17 (FIG. 6) is outlined via 77 (FIG. 6). Inside the extractor 17, there is a 90° degree angle reducing elbow fitting 89 (FIG. 6) that is the interior continuation part of male inlet 41 (FIG. 6). Male inlet 41 (FIG. 6) and elbow fitting 89 (FIG. 6) are made of titanium and welded together; or can be assembled together via treads (thread not shown) before they are welded to the housing 17 (FIG. 6). Reducing elbow fitting 89 (FIG. 6) is then coated with graphene or gold plated. The end part 100 (FIG. 6) of reducing elbow fitting 89 (FIG. 6) is pointing to the bottom inside extractor 17. Said end part 100 (FIG. 6) as female threads for connecting an air bubble diffuser, also called a gas diffuser (known to the art). Said air bubble diffuser (not shown) is preferably; a tubular air diffuser (known to the art); having a stainless steal male threaded adapter at one end (that screws into female threaded end part 100 (FIG. 6)); followed by a numerously perforated flexible rubber membrane tube that is sealed by a stainless steal cap at the opposite end. Said membrane tube is sufficiently long to form a coil at the bottom inside the extractor 17. This way said mixture incoming from tube 40 (FIG. 6) is in essence mixed more appropriately by the bubble diffuser. Said compound(s), and/or drug(s) 16 are placed over the said bubble diffuser. This way a better assimilation is assured between the incoming mixture from tube 40 (FIG. 6); that passes through the bubble diffuser and reaches the compound(s), and for drug(s) 16. Water and steam along with the said dry gases are all permitted to traverse the numerous perforations of the said flexible rubber membrane tube.

Incoming from said bubble diffuser, hot water and steam then mixes with the compound(s), and for drug(s) 16 to form an hydrolysis reaction (chemical breakdown of the compound(s) and/or drugs(s) 16). Other molecule(s) mentioned earlier comprising: (carbon base molecules, organic molecules, neutral current charge molecules) are for the most part devoid (absent) of a positive or negative current charge; and therefore not captured by the superconductive wire 23 (FIG. 6). However said steam (vapor) deriving from hot water; along with the other ($H_2O$) derived steam incoming from tube 40 (FIG. 6) are both used for capturing said (carbon base molecules, organic molecules, neutral current charge molecules). Said steam 53 (FIG. 6) is in motion and rises up the extractor 17 (steam is driven up by heat and pressure from incoming contents of tube 40 (FIG. 6)), and converging and passing with said wire 23 (FIG. 6) through a female treaded titanium outlet 44 (FIG. 6) that is welded to the side of the extractor 17, found below the cover 38 (FIG. 6). A pipe 45 (FIG. 6) (tube) made preferably of titanium having diamagnetic material(s) graphene coated, or gold plated interior. The exterior of said titanium pipe 45 (FIG. 6) as male treads at both ends. One end; counterclockwise male tread 46 (FIG. 6) screws into female counterclockwise treaded outlet 44 (FIG. 6) (female tread not shown) of the extractor 17. Said titanium pipe 45 (FIG. 6) links the extractor 17 to the housing via the structural wall of the base member 18. Herein clockwise male tread 70 (FIG. 6) of titanium pipe 45 (FIG. 6) enters via a clockwise female treaded inlet 73 (FIG. 6)(female tread not shown) of p-trap 47 (FIG. 6) that opens inside the base member 18. The said counterclockwise and clockwise threads permit screwing (joining both ends of 45 (FIG. 6) with 44 (FIG. 6) and 73 (FIG. 6) simultaneously. Each end 74 (FIG. 6) and 75 (FIG. 6) of said superconductive wire 23 (FIG. 6), are each connected to a separate terminal: wire end 74 (FIG. 6) with terminal 71 (FIG. 6), and wire end 75 (FIG. 6) with terminal 72 (FIG. 6). Both terminals are fixed inside the p-trap 47 (FIG. 6) wall. Each said terminals are made of metal example: iron or gold. Said p-trap 47 (FIG. 6) is made preferably of titanium having diamagnetic material(s) graphene coated, or gold plated interior) that is submerged by incoming water from the base member 18. Therefore wire 23 (FIG. 6) is in contact with the magnetism induced water 18a inside the base member 18. The said titanium pipe 45 (FIG. 6) and outlet 44 (FIG. 6) of the extractor 17 are positioned above the p-trap 47 (FIG. 6) preventing water reflux from entering. Wire 23 (FIG. 6) has occasional plastic wire separators also called wire grip separators (not shown) from outlet 44 (FIG. 6) that ends just before terminal 71 (FIG. 6) and terminal 72 (FIG. 6).

The titanium pipe 45 (FIG. 6) containing the superconductive wire 23 (FIG. 6) is cooled via the exterior causing a catalyst reaction inside (similar to crystals forming in the Atmosphere) when the hot steam containing molecule(s), ionic compound(s), molecular ion(s) and hot water, dry gases (air, $CO_2$, and oxygen) converges with the magnetic field charged superconductive wire 23 (FIG. 6). And further colliding with the cooled air within the (diamagnetic) titanium pipe 45 (FIG. 6); causing convection as the cooled air descends the extractor 17 releasing nano particles from the solid compound(s), and/or drug(s) 16 (FIG. 6), in the extractor 17 (FIG. 6); captured by the rising hot steam 53 (FIG. 6). The building pressure incoming from the extractor 17 (FIG. 6); created by the hot water, steam, and dry gases (air, $CO_2$, and oxygen) coming from tube 40 (FIG. 6) enabled this mixture to move into the housing (base member 18 (FIG. 6) toped by its cover); and dispersing inside; and also contained in bubbles 52 (FIG. 6) breaking the water's surface 18a (FIG. 6) as water-vapor mist containing the said mixture, disperses between water's surface 18a(FIG. 6), and the covers underside, inside the housing. To converge with, living tissues, and respiratory track of the patient 19, placed inside the housing (base member 18 toped by the cover).

The extractor 17, system as a hole benefits therapeutic assimilation, and bioavailability, of nutrients and further benefits as a preventive measure to alleviate from the occurrence of molecule(s) fragmentation, and (is to some extent) similar to growing molecule clusters from a particle (dust) in the upper Atmosphere, Or ionic crystals much like snowflakes are formed (grow). The molecule(s) and ionic compound(s) molecular ion(s) empties inside the base member 18 (mostly lacking solid compounds that remain in the extractor 17) along with dry gases (air, $CO_2$, and oxygen) and vapor laden with molecule(s) and ionic compound(s), molecular ion(s) 54 (FIG. 6).

Therefore because the said molecules, and ionic compounds, molecular ions, are so "small", they can easily pass into living tissues, and are further helped by the magnetic field produced by the housing (base member 18, and cover); making the present embodiment unique. The present embodiment is therefore providing molecular therapy closer in approach to natural means. In the present embodiment, the use of said dry gas (Air) from tube 40 (FIG. 6) entering the extractor 17; is further used to add some pressure that creates movement of the preferred mixture (molecules, ionic compounds, molecular ions) to further enter titanium pipe 45 (FIG. 6) and reach the patient 19, inside the housing (base member 18 (FIG. 6) toped by its cover). Furthermore magnetism induced water-vapor mist diluted the skins (relaxes the hydrophobicity on skin) cellular tissues of patient 19; so that assimilation, and bioavailability, of nutrients is assured between water 18a and the underside of the housing cover wherein the skin that is not submersed in water 18a can still receive said nutrients (molecules, and ionic compounds, molecular ions).

The said titanium pipe 45 (FIG. 7) is cooled using pressurized liquid ($CO_2$) coolant circulated in 1.4 millimeter interior diameter size tubing 48 (FIG. 7), made of high pressure stainless steel having maximum design pressure of 100 bar, that forms a tight coil arrangement 56 (FIG. 7) around at least part (approximately ⅔rds) of the exterior of said titanium pipe 45 (FIG. 7). And the ensemble is coated or covered via the exterior with thermal polytheretherketone film or equivalent thermo insulator (not shown). The coolant tube 48 (FIG. 7) is connected to an electric solenoid valve 49 (FIG. 7), to control flow pressure of said liquid cot, and as a precautionary measure before it (tube 48 (FIG. 7) enters the base member 18 (FIG. 7) via a female treaded outlet 50 (FIG. 7) connecting the solenoid valve 49 (FIG. 7). Said solenoid valve 49 (FIG. 7) is controlled by the sequencing unit 15 via wire 51 (FIG. 7) (wire only shown in part). Said liquid ($CO_2$) coolant inside coolant tube 48 (FIG. 7) flows in direction of the base member 18. The coolant tube 48 (FIG. 7) forming a coil 56 (FIG. 7) around the titanium pipe 45 (FIG. 7) where the coolant tube 48 (FIG. 7) then deviates away from the extractor 17. The ($CO_2$) liquid coolant after having circulated within a network of tubing 24 (FIG. 2) located inside layer 24a (FIG. 2) of the housing structure; then exits the housing; to recovery storage tank(s). And fresh liquid ($CO_2$) from pressurized storage tanks is filtered (via a cryogenic filter housing containing a filter cartridge) and recirculated back into the housing (base member 18, and cover) via tubing 48 (FIG. 7). Or preferably said cryogenic liquid carbon dioxide ($CO_2$) coolant is furnished via laboratory, or hospital facility that also providing recovery tanks. Furthermore some industrial facilities provide the service of "recovery/processing" of said cryogenic liquid carbon dioxide ($CO_2$) coolant. Liquid hydrogen (H) cooling, is also known to the art; however is not as safe a cryogenic coolant, but may and can be an alternative where carbon dioxide ($CO_2$) liquid coolant is unavailable.

To help support the weight of the extractor 17. A plastic leg, or block could and may be used to prevents adding weight (stress) to the structure of the base member 18, that may otherwise occur. In one example: the extractor 17 (FIG. 6) sits on a plastic supporting plate 91 (FIG. 6) Plate 91 (FIG. 6) attaching to a plastic male treaded rod 92 (FIG. 6) via a grooved clevis pin 98 (FIG. 6) that is set in same size hole 99 (FIG. 6) in the center of one end of rod 92 (FIG. 6). Plate 91 (FIG. 6), is held in place using an external retaining ring 96 (FIG. 6) that fits onto rod 92 (FIG. 6) via groove 97 (FIG. 6). At the opposite end of the rod 92 (FIG. 6), that screws into a female treaded rectangle 93 (FIG. 6) that sits on a plastic footing plate 94 (FIG. 6) that sits on the floor 95 (FIG. 6). This way the rod 92 (FIG. 6) can move supporting plate 91 (FIG. 6) up and down to compensate for distance between the floor 95 (FIG. 6), and the extractor 17 (FIG. 6). Said pin 98 (FIG. 6) is press fit into hole 99 (FIG. 6) of rod 92 (FIG. 6), for a snug fit. Or the clevis pin 98 (FIG. 6) can and may be glued into place or molded into hole 99 (FIG. 6).

However said extractor 17, via the titanium pipe 45 (FIG. 7) can connect, enter, be attached to other shape(s) of housings, then shown in FIG. 1, and provide other forms of treatments, application(s) as specified earlier.

Some examples: using male tread 70 (FIG. 6) of titanium pipe 45 (FIG. 6) that enters a female treaded plumbing fitting (not shown) having two terminals inside; that is one for each wire ends 74 (FIG. 6) and 75 (FIG. 6) for connecting wire 23 (FIG. 6), comparably done with; for example: terminals 71 (FIG. 6) and 72 (FIG. 6) of P-trap 47 (FIG. 6). Said female fitting in turn is connected to:

a magnetic field induced metal pipe plumbing assembly; or a non magnetic field induced pipe plumbing assembly; that can in turn connect with a magnetized or non magnetized water temperature control unit: comprising: thermostatic mixing valve, hot, and cold water inlet(s), and/or outlet(s), plumbing valve, water mixers chamber(s), steam/cold water mixer(s), plumbing assembly; or any other shape of (housing), having a cover or not. From herein these described housings would disperse $H_2O$-vapor laden with molecule(s) and ionic compound(s) contained in, water, $H_2O$-steam, water vapor (mist) coming from the titanium pipe 45 (FIG. 6) via any: shower head(s), or water sprinklers, water jet(s), or steam jet(s), plumbing valve, Gas/Air diffuser. For instance if the apparatus for example is a shower, green house, Jacuzzi, or pool sauna, aquarium, hydroponic container, or any other housing as described in the first paragraph of FIG. 1. For any vegetation treatments; dry gases (air, $CO_2$, and oxygen) can and may be provided in the same way as demonstrated in (FIG. 6), via titanium pipe (45). And further more; quantities of dry gases (air, $CO_2$, and oxygen) may differ greatly for treating vegetation compared to quantities for a patient 19. One example: providing dry gases (air, $CO_2$, and oxygen) via titanium pipe (45) to a plumbing fitting for connecting a gas/Air diffuser submerged in a water environment in contact with plant roots inside a hydroponic container.

Notes: Titanium is light weight, durable, and is a good corrosive resistant metal. And is used throughout many parts of the apparatus.

More then one valve may be used for controlling incoming said dry gases and said hot water and $H_2O$-steam that supply tube 40 (FIG. 6).

Cryogenic tape for all cryogenic applications and, Teflon plumbing tape are used for leak proofing all threaded fittings of the apparatus.

Not to be confused with said dry air that feeds tube 40 (FIG. 6).

An alternative to using electric solenoid valve(s). Are pneumatic solenoid valve(s) using compress air to operate mechanically, and in turn is controlled by electric current via wire(s) linking the sequence unit 15. Compressed air for operating a pneumatic valve is for example: via a facility (laboratory or hospital) where a service wall outlet providing compressed air is available to operate a pneumatic type valve. Or air provided by linking via the tank of an air compressor, or pressurized air from a cylinder storage tank. Pneumatic flexible tubing having connectors links the air supply to operate the said pneumatic valve(s).

FIG. 2, shows the structural composition of one form of housing to FIG. 1 comprising: base member 18 (FIG. 1) and said cover (not shown) according to the present embodiment, wherein the exterior structure wall of said housing has magnetic barrier properties for preventing exterior frequencies, exterior currents, and exterior magnetic fields, from penetrating, or interfering with the prescribed functions of the housing. And that comprises: non conductive material(s), diamagnetic material(s), para-magnetic material(s), for example: rubber, plastic, silicon, stainless steel, graphene or a combination thereof. For example: exterior paneling 20a (sheets) preferably comprise: diamagnetic graphene oxide coated (used as a barrier) stainless steel that can bend somewhat and folded using a press to form and cover the exterior of the housing. Paneling 25a (sheets) are panels that can bend somewhat or be folded using a plastic hot press tool known to the art). The panels 25a are made of plastic and of magnetic compounds (magnetic compounds is explained in more detail further on) that makes up the interior surface wall of the housing (of base member 18 and cover) to FIG. 1. Panel(s)

25*a* meets between the cover and base member 18, and fits under the exterior paneling 20*a*, that is folded 90° degree (angle) along and near 63, the exterior perimeters of panel 20*a*). Any spacing left between exterior panels or where exterior/interior panels meet are filed with removable-flexible (T shaped) rubber molding. Any spacing left between joining interior panels is filed using two-part epoxy resin or filed using plastic welding techniques (plastic welding with plastic rods known to the art). Interior layer 20 adjacent the exterior wall paneling 20*a* is a thermal layer made of silicon (aerogel) to further insolate the prescribed functions of the housing. In another aspect the interior wall structure of both the base member 18 (FIG. 1) and cover (cover not shown) of the housing for treating a subject 19 (FIG. 1); are carbon dioxide ($CO_2$) liquid cooled via layer 24*a*. This amplifies the performance of each electromagnets, magnets, and electronics aspects of the housing part to (FIG. 1) of the apparatus; as electrical current flow is optimized, and is well known to the art. Both the semi-thermo layer 25 adjacent to the back of panel 25*a* of the housing; and the thermo layer 20 adjacent the back of surface of exterior panel 20*a* of the housing are maintained relatively warm, between 20° and 30° Celsius (room temperature). This is achieved via a diamagnetic material silicon (aerogel) that is also a thermal insulator. Layer 25 is a semi-thermo insulator layer because the layer is interrupted by each electromagnets inside; that are flush to the back surface of panel 25*a* of both the base member 18 (FIG. 1), and cover. Each electromagnet is spaced with a thin coating approximately between 1 and 2 nanometers thick of diamagnetic graphene oxide, (used as a barrier) that can be applied to the back surfaces 82 (FIG. 8) of panel 25*a*. And then covered with said silicone (aerogel) as thermal insulator approximately between 2 and 10 millimeters thick.

Panel 25*a*, wherein the surface is covered with a plurality of round holes 62 (FIG. 8). A space 87 (FIG. 8) is provided between each holes 62 (FIG. 8); forming rows. Each of the holes 62 (FIG. 8) are for receiving each a round pin shaped magnets 58 (FIG. 8) having flat ends 79 (FIG. 8) and 86 (FIG. 8). The magnets 58 (FIG. 8) (match fits the holes 62 (FIG. 8)) are placed in the holes 62 (FIG. 8) flat end 86 (FIG. 8) first; and pushed all the way inside panel 25*a*; as indicated by 83 (FIG. 8), to become part of the panel 25*a*(FIG. 8). Both ends 79 (FIG. 8) and 86 (FIG. 8) of each magnets 58 (FIG. 8) respectively come flush; that is: 79 (FIG. 8) with back surface (82 (FIG. 8) and 86 (FIG. 8) with the inside housing surface 84 (FIG. 8) of panel 25*a*(FIG. 8).

Before the plurality of magnets 58 (FIG. 8) are placed inside the plurality of holes 62 (FIG. 8); the chosen magnetic field emitted by each magnet 58 (FIG. 8) must be determined ahead of time (that is positive or negative magnetic field). For example: if the chosen magnetic field is to be positive; it is important therefore that the flat end 79 (FIG. 8) of each magnets 58 (FIG. 8) is of the opposite pole (positive or negative) then the pole of the core within each electromagnet 60 (FIG. 8) emitting the magnetic field via flat end 80 (FIG. 8). Because these ends; flat end 79 (FIG. 8) and flat end 80 (FIG. 8) will engage and align; that permits the magnetic field created by the electromagnet 60 (FIG. 8) (that is positive or negative magnetic field) to pass through magnet 58 (FIG. 8) inside holes 62 (FIG. 8), pass inside housing surface 84 (FIG. 8) to enter the housing interior (base member 18 and cover). The preferred magnetic field inside the housing (base member 18 and cover) is to have one magnet 58 (FIG. 8) produce positive magnetic field; and an other magnet 58 (FIG. 8) producing negative magnetic field and so on in checker board fashion from row to row of each panel(s) 25*a*.

Said magnets 58 (FIG. 8) are made of para-magnetic ceramic materials; matching the para-magnetic materials of the core inside the electromagnets 60 (FIG. 8). Core and it's para magnetic materials described in (FIG. 1). However flat end 86 (FIG. 8) of the magnets 58 (FIG. 8) are iridium metal coated, to protect the magnets 58 (FIG. 8) from corrosion since they are flush with the interior surface 84 (FIG. 8) of paneling 25*a* (facing inside the housing). Unlike electromagnet 60 (FIG. 8) that do not contain any iridium. The iridium coating is a para-magnetic metal that is very hard, and is very high corrosion proofing that protects the magnet 58 (FIG. 8); and is furthermore considered a low health hazard (known to the art). The magnetic field producing end 80 (FIG. 8) of the electromagnet 60 (FIG. 8) is in contact and in line with the said magnet 58 (FIG. 8) matching in size and shape for providing good contact. A plastic flanged bushing 59 (FIG. 8) (flanged at one end); fits flange 78 (FIG. 8) first over the electromagnet 60 (FIG. 8), where the back flange surface 81 (FIG. 6) of flange 78 (FIG. 8) is (in contact) flat to the back panel surface 82 (FIG. 8) of panel 25*a* (FIG. 8), with the electromagnet 60 (FIG. 8) inside the plastic bushing 59 (FIG. 8; and (the electromagnets 60 (FIG. 8)) comes in contact flush with the flat end part 79 (FIG. 8) (flat end part 79 (FIG. 8) not iridium coated) of magnet 58 (FIG. 8) (that is at the back surface 82 (FIG. 8) of panel 25*a*(FIG. 8)). This way magnets 58 (FIG. 8) becomes electromagnets whenever the electric current to the electromagnets 60 (FIG. 8) is activated; and magnets 58 (FIG. 8) returns to a simple magnets whenever power is cut-off to electromagnets 60 (FIG. 8). The flanged part 78 (FIG. 8) of plastic bushing 59 (FIG. 8) is held
in place with plastic lock fasteners via pre drilled holes, or can also be held using plastic screws into the back surface of 25*a* via pre threaded holes not crossing pass interior surface 84 (FIG. 8) of panel 25*a*. Said flanged part 78 (FIG. 8) can and may be held in place with a two-part epoxy resin. A layer of silicone (aerogel) is applied as a thermal barrier over the graphene coating and between and overlapping the flanged part of plastic bushings 59 (FIG. 8). Said silicone must not form a layer that covers pass the non-flanged ends 85 (FIG. 6) of bushings 59 (FIG. 8) so as not to cover the back ends 88 (FIG. 8) of the electromagnets 60 (FIG. 8). This way the circulating liquid co2 coolant in tubes 24 is permitted to cool the electromagnet 60 (FIG. 8), but not the space 87 (FIG. 8) of panel 25*a*. This keeps the inside housing (beyond surface 84 (FIG. 8) wherein the subject is) from cooling. Plastic bushings 59 (FIG. 8) are convenient, since the electromagnets 60 (FIG. 8) match fit inside 59 (FIG. 8) keeping the electromagnets 60 (FIG. 8) in place, yet can still easily be removed for maintenance. Part of an electromagnet wire is shown 61 (FIG. 8).

Said magnets 58 (FIG. 8) provide a clean and safe environment for patient 19 (FIG. 1) inside the housing (base member 18 (FIG. 1) and cover); since there are no coils, or electromagnets, or wires inside with patient 19 (FIG. 1). Patient 19 (FIG. 1) is further protected by said iridium coating on flat end 86 (FIG. 8) of the magnets 58 (FIG. 8) that is facing inside the housing (base member 18 (FIG. 1) and cover), and therefore patient 19.

The qualities of iridium (Ir) and different methods for making an iridium coating, for example such as described with
"WANGPING WU and ZHAOFENG CHEN, Growth mechanism of polycrystalline Ir coating by double glow plasma technology. Collage of Material Science and Technology, Nanjing University of Aeronautics and Astronautics, Nanjing 210016 China. Acta Metall. Sin. (Engl. Lett.) Vol. 25 No. 6 pp 469-479 December 2012"; is included herein as reference.

A copper or brass materials flange bushing can and may be used instead of the preferred, plastic bushing 59 (FIG. 8). However plastic is preferred for having electric current insulator qualities and non magnetic insulator qualities; and is less likely to interfere with prescribed magnetic field emitted by the housing (base member 18 (FIG. 1) and cover).

Some examples for making or providing a plastic panel (panel 25a) with magnets is described: a semi flexible plastic panel is perforated from (surface to surface) with (press fit) round holes. The holes can be made using preferably a press. Or using a press drill. A space is provided between each holes creating rows horizontally, and vertically along the surface of the panel. Then a graphene oxide coating is applied to the back surfaces of the panel. A two-part epoxy resin is mixed and a coating is applied inside the holes. Round pin shaped magnets having flat ends are inserted flat ends first in each holes each hole containing a magnet, with the flat ends (of the magnets) flush with both surfaces of the panel. Once the resin is set it will create a firm leek proof seal around the magnets preventing seepage of any liquids inside the housing from entering inside the structure via the holes containing the magnets. Any excess said two-part epoxy resin that may cover the ends of the magnets can be removed using sand paper.

Or; instead of using a said two-part epoxy resin. Both surfaces of said panel(s) can be heated on a flat hot press (known to the art) with the said magnets inserted inside the said holes. This will seal (bind) the ends of the magnets with the plastic panel, leek proofing the holes. Or still the two-part resin coating is applied inside holes, then the magnets are inserted inside and the said resin is left to set. Then the said hot press is used on both surfaces of the panel has described above to further seal the said the magnets inside the panel. A sand paper is used to remove the excess resin from the ends of each magnets. The said diamagnetic graphene coating can be applied before; or preferably after the magnets are set (final set) inside the panel.

Between layer 25 (containing electromagnets 60) and to the electronic components layer 22 (containing cables wires 22a, and circuit boards); a space is provided in layer 24a within the structure. Herein cryogenic tubing for pressurized liquid carbon dioxide ($CO_2$) is circulated in 1.4 millimeter interior diameter size tubing 24 and tubing 48 (FIG. 7) (that is circulated outside the housing). Said tubing 24, and 48 (FIG. 7) is made of high pressure stainless steel having maximum design pressure of 100 bar. A carbon dioxide ($CO_2$) cryogenic filter(s) (not shown) is found between the CO2 liquid supply (not shown) and the tubes 48 (FIG. 7) before entering the base member 18 (FIG. 1) and the cover; to prevents clogging by particles that could lodge in the valve fittings. High pressure stainless steel female treaded electrical solenoid valves (one example shown 49 (FIG. 7)) are found on both entries and exit tubes of both the cover and the base member 18 (FIG. 1). Said valve(s) example 49 (FIG. 7) are to prevent accidental pressure overload within the housing and to control temperature range of said circulating coolant. For example: if the solenoid valves (one example 49 (FIG. 7)) are shut. Then the coolant contained in tubing 24 inside the structure layer 24a that is not circulated will warm up faster generated by heat from the electromagnets 60 (FIG. 8) inside layer 25 that generally produce heat and also from layer 22 containing electronic circuit boards that generally produce heat. Cooling electronic(s) for greater conductivity, and higher para-magnetic, diamagnetic, and electromagnetic performances. Requiring lower magnetic frequencies; and therefore shorter time exposures under magnetic field to living tissues. The coolant temperature range is kept approximately between 5° Celsius, and −40° Celsius and is measured via electronic temperature sensors within layer 22; (on the circuit boards) and the temperature readings are displayed on the computer monitor 11 (FIG. 1). Each tubes (example 48 (FIG. 7) providing ($CO_2$) liquid coolant that enters/exits the base member 18 (FIG. 1) and cover (for the said cover: via flexible cryogenic tubes (not shown)). Each tube (example 48 (FIG. 7) entering a separate electrical solenoid valves (one example of valve 49 (FIG. 7)). Each electrical solenoid valves 49 (FIG. 7) is connected via wire (one example wire 51 (FIG. 7) shown in part) to; and controlled by the sequencing unit 15 (FIG. 1). The coolant exits the base member 18 and cover; to be recycled, (processed) then recirculated back into the base member 18 and cover. Tubing 24 serves to circulate carbon dioxide ($CO_2$) liquid coolant throughout the structure of both the base member 18 (FIG. 1) and cover; (linking a network of tubing 24 inside the housing) approximately one tube 24 for each row of electromagnets 60 (FIG. 8). A vacuum retracts condensation from building inside the structure of both cover and base member 18; each having a male connecting outlet at one end, and each fitted with a flexible tubes connected to a (y) fitting in turn connected to a single vacuum for drawing air from both cover, and base member 18. Air is drawn via vent holes; one on each sides of; and at the opposite ends of both, the base member 18 and cover, via the layer 24a. The condensation is measured by electrical humidity sensors on the circuit boards inside layer 22 (not shown) activating the vacuum when condensation needs to be evacuated. And humidity readings are displayed on the computer monitor 11 (FIG. 1), (vacuum system is not shown). Panel 90, and panel 21a are perforated with rows of holes from surface to surfaces using a press to make the holes. Approximately each hole is between 5 and 10 millimeters wide and an equal amount of panel is left in between each holes so that the panels remain sturdy. This enables tubing 24 to cool adequately electromagnets 60 (FIG. 8) inside layer 25 and circuit boards in layer 22.

Another important aspect are
plastic coated cables used to link one unit to the other; demonstrated by arrows (lines) between units to FIG. 1. Each said plastic coated cables contain a plurality of wires for electronic connections.

Said cables further comprise: male connectors having an equal amount of connecting metal pins for each wire; that connect to female connectors having an equal amount of metal holes for receiving male connectors. Plastic coated cables are further used to link units to FIG. 1, with the housing (base member 18 and cover); and still further used inside the housing to link with the circuit boards forming a network of plastic coated cables for example: plastic coated cables 22a inside layer 22 of the housing.

Micro processors located on said circuit boards inside layer 22 control the electromagnets inside thermal layer 25, and further control humidity, and temperature within the structure of the housing via: humidity sensors, and temperature sensors also located on said circuit boards.

Plastic cable clamps having snap-in mounting means, to hold cable wires, and plastic wire saddles having snap-in mounting means to hold wires (all are known to the art) are attached inside the housing structure, via pre drilled or press holes (not shown) in plastic panel 21a. In the same way circuit boards are held in place using snap-in stand offs (known to the art) to attach with panel 21a. Tubing 24 is held to plastic panel 90 using plastic tube clamps having snap-in mounting means via pre drilled or press holes (not shown) in plastic panel 90.

Plastic is preferred for magnetic, and electric current insulator properties. For extra support, stainless steal screws are used for exterior paneling 20a to hold with the interior panels that have plastic spacers having pre treaded screw holes only for engaging said stainless steal screws located in the interior housing corners. All other plastic spacers (cylindrical shaped spacers having flat ends with a hole in the middle that traverses one flat end to the other known to the art) are placed between interior panels (for example: between panel 90 and panel 21a) in key points (spaced in the middle, and spaced along interior perimeters). And are held in place between panels by plastic snap lock supports (known to the art) traversing inside spacer holes to engage one panel to the other via pre drilled or press holes of each panels (not shown). The only exception is with panel 25a, that are screwed (using plastic screws) via interior surface 84 (FIG. 8) into female treaded spacers located on the opposite surface 82 (FIG. 8) and further held by plastic screws incoming via panel 90. The screw heads of surface 84 (FIG. 8) (not shown) of panel 25a; are sealed using two-part epoxy glue. The above described assemblage lends support to the entire housing structure.

Rubber or plastic washers can and may be used with said stainless steal screws in the interior housing corners.

The housing (base member 18 (FIG. 1) and cover) can and maybe transported on a floor using a dolly, that is well know to the art. The housing (base member 18 (FIG. 1) and cover) can further be left permanently on a said dolly since; industrial type dolly's usually come equipped with stock or optional swivel LOCK caster wheels also known to the art.

Figure 3:
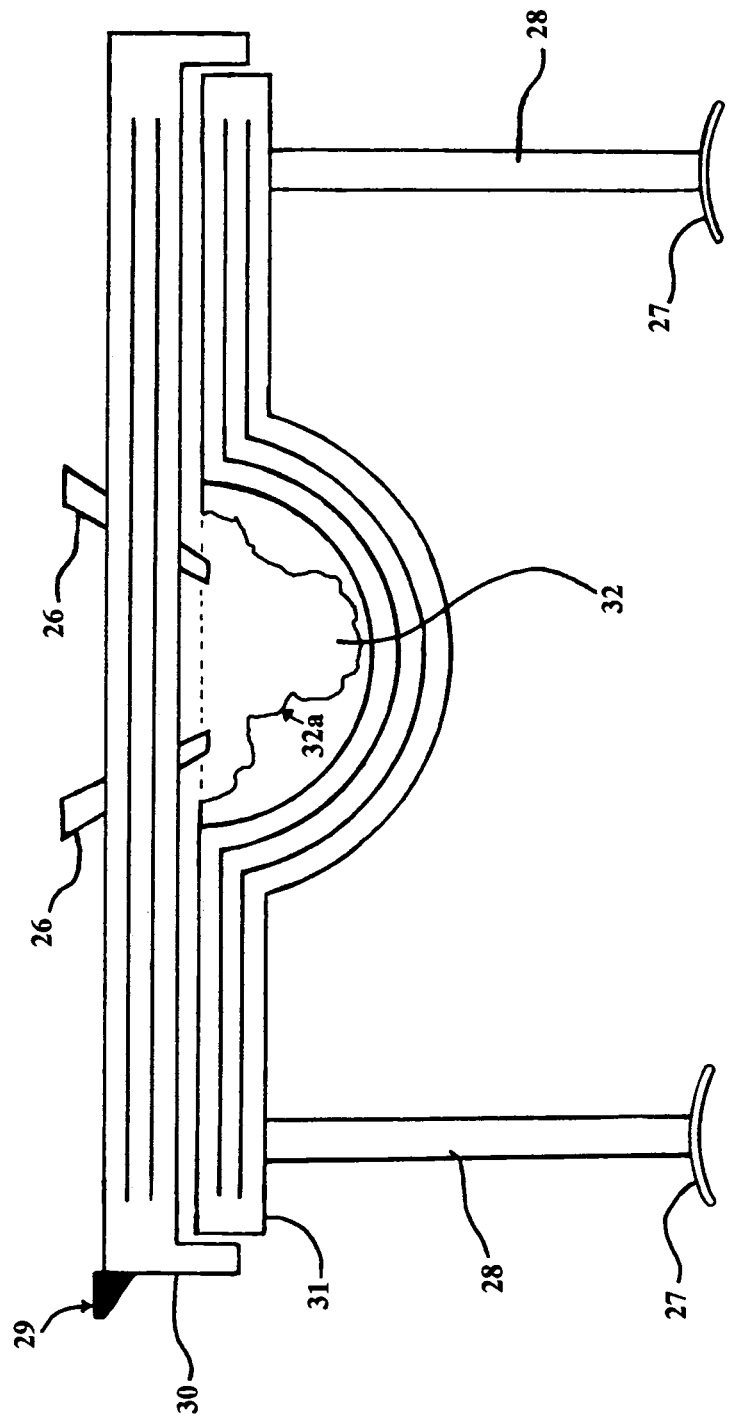
FIG. 3 is an exploded cross-sectional view of a housing (cover and base member) for controlling, very small organism(s), such as a living cell according to another embodiment of the present invention.
Figure 4:
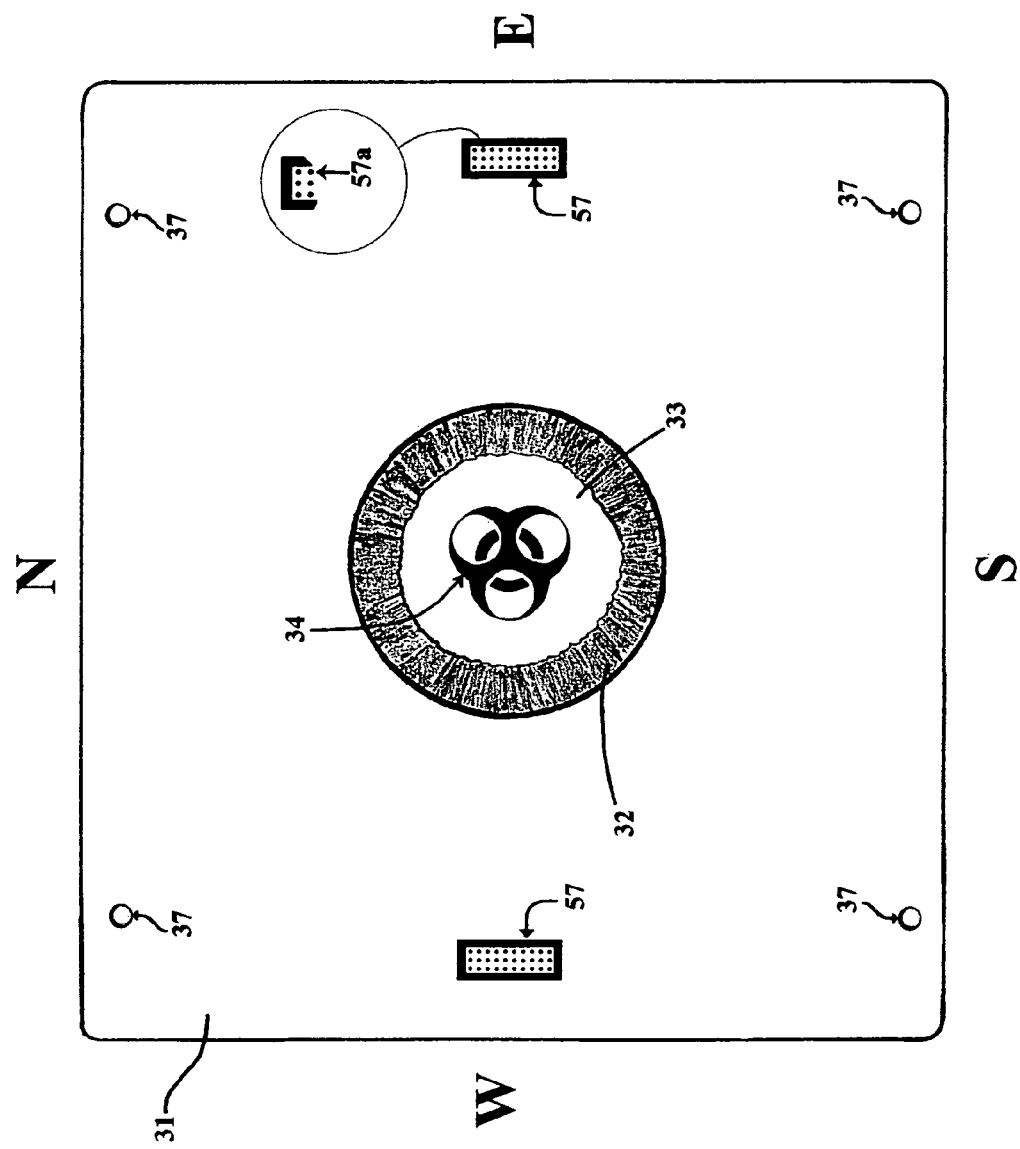
FIG. 4 shows an above view of a base member of a housing apparatus for controlling very small organism(s), to (FIG. 3), without the cover.

FIG. 3, shows a magnetic conductive housing FIG. 3, for controlling, very small organism(s). One example: such as a living cell 34 (FIG. 4). The housing FIG. 3 has both a base member 31, and a cover 30. The base member 31 having support columns 28 (made of graphene exterior coated titanium metal), that rest upon leveling mounts 27. The base member 31 has a central bowl shaped cavity 32 (an open fractured view delimited by outline-part doted line 32a showing inside the bowl shaped cavity 32 FIG. 3), and a non fractured from above view of the cavity 32 (FIG. 4). Water 33 (FIG. 4) is placed inside the base member cavity 32 (FIG. 4), wherein a living cell for example: can be placed in the said water 33 (FIG. 4), and be controlled physically, inside-out, using very low strength magnetism between 0.01 microtesla (this is well below "45-47 microtesla" approximately earth's magnetic field) and 1 Tesla. Both the base member 31 and cover 30 contain nanotubes, between (4 and 32) nanotubes each. However nanowires may and can be used instead of said nanotubes. Said nanotubes, and nanowires are preferably made of iridium (Ir) nanoparticals, iridium oxide, and may further contain platinum oxide. Each nanotube in the base member cavity 32 is positioned pointing (like needles surrounding a half sphere), In the underside of the cover 30 above the cavity 32 of base member 31; herein nanotubes are pointing from above, and directed at the cavity 32 below. Each said nanotube in the cover 30 and in the base member 31 are sandwiched in Diamagnetic material(s), graphene; but leaving sufficient part of the ends of said nanotubes bare (uncontaminated) by the said graphene. This way each nanotube is positioned to control a unique part of the central cavity 32; and therefore a living cell 34 (FIG. 4) if placed in the water 33 (FIG. 4), inside the base member cavity 32. This permits the cell to easily be maneuvered, given the hydrophobicity change of water under magnetism (as described in the Background of the invention). Each of the nanotubes are controlled by para-electromagnets (one para-electromagnet for each said nanotube) approximately 5×5 millimeters wide or smaller. And each said para-electromagnets is spaced one from the other with graphene. Each of the nanotubes is in direct contact (one or more nanotube per electromagnet) with each electromagnets, (that is the electromagnet is in contact with one end of the nanotube) and the other end of the nanotube extends to the base member cavity 32. Wires can, and may be used with, or instead of nanotubes. For example: high-temperature superconductor nanowires, able to reach the base member cavity, The cavity is approximately 0.5 millimeters thick, and made of diamagnetic materials. For example: graphene, or gold. It is important that the nanotubes or nanowires are flush with or slightly cross into the interior wall of cavity 32; and remain uncontaminated by the diamagnetic materials graphene or gold. This way the magnetic field emitted by the said nanotubes, or nanowires is not altered by the diamagnetic composition (of the structure wall) of the cavity 32. The sequencing unit 15 (FIG. 1) connect to the housing FIG. 3 using multi-wire cable having a male connector(s) via port 29, having a female connector(s). Port 29 is located on one sides of cover 30 (FIG. 3). From the inside of port 29 other multi-wire cables lead on from a connector(s) that engage circuit boards inside the structure of cover 30 connecting female connectors 58 (FIG. 5) that are flush with the underside surface of cover 30, to engage male connectors 57 (FIG. 4) slightly raised through the top surface of base member 31. In turn said male connectors 57 (FIG. 4) are connected to circuit boards inside the structure of base member 31. This way the entire housing is conductively linked and controlled by the sequencing unit 15 (FIG. 1).

Figure 5:
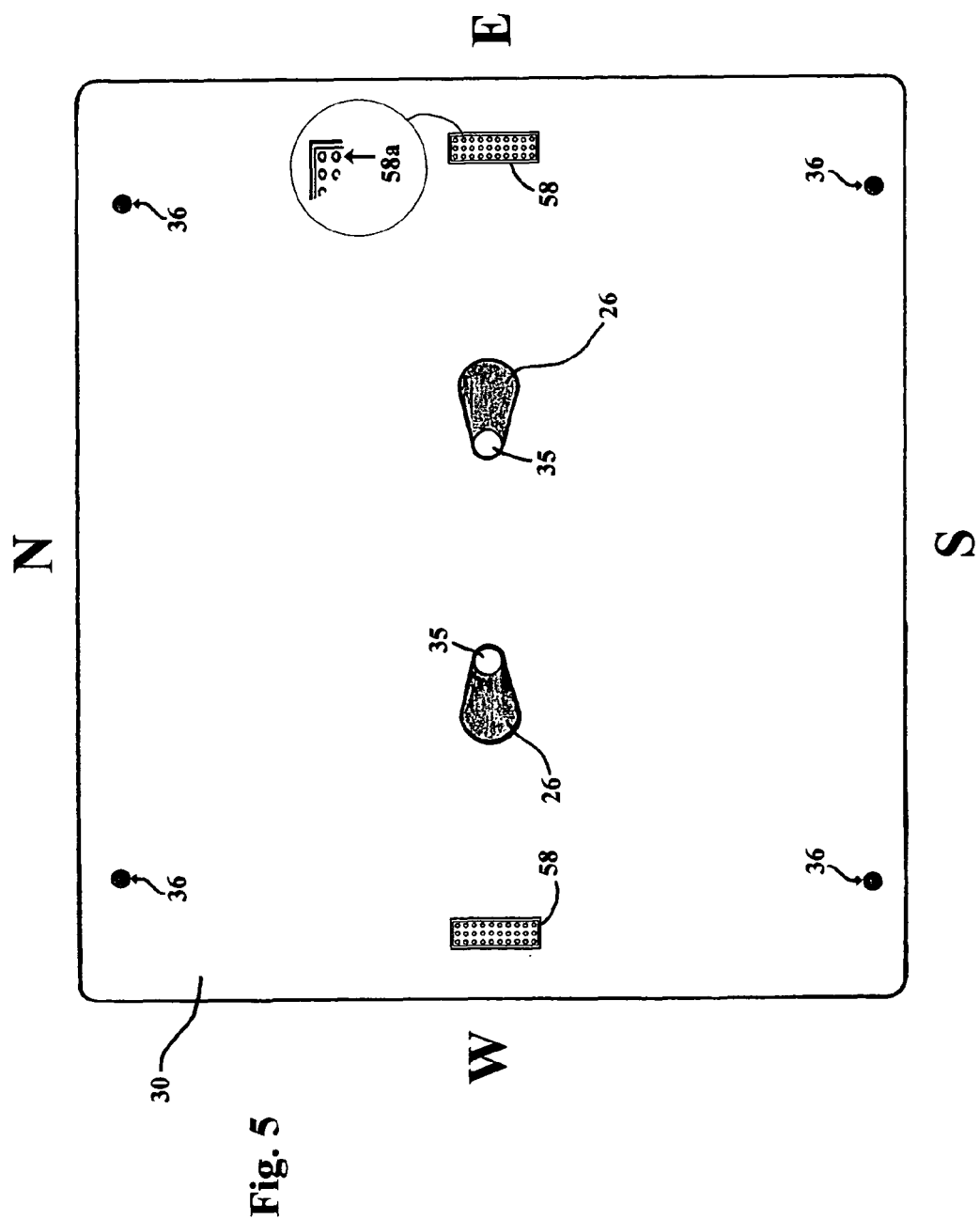
FIG. 5 shows an above view of the underside of the cover for the housing apparatus for controlling very small organism(s), to (FIG. 3).

Electrical power, and sequencing commands received from the sequencing unit 15, control circuit boards inside the structure of cover 30, and inside the structure of base member 31 that control the electromagnets, in turn the nanotubes. The cover 30 sits on top the base member 31 wherein they both align perfectly together via pins 36 (FIG. 5) along a perimeter in the underside of said cover 30, that enter holes 37 (FIG. 4) along the perimeter in the top surface of the base member 31. A close up view is shown of pins 57a (FIG. 4) and of holes 58a (FIG. 5).

The qualities of iridium (Ir) as mentioned in FIG. 2, further applies to nanotubes and nanowires of FIG. 3. In a different example: the qualities and the making of iridium oxide nanowires is described with "FENGYAN ZHANG, ROBERT BARROWCLIFF, GREG STECKER, WEI PAN, DELI WANG and SHENG-TENG HSU. Synthesis of Metallic Iridium Oxide Nanowires via Meta Organic Chemical Vapor Deposition. Sharp Laboratories of America, Inc. 5700 NW Pacific Rim Blvd, Camas, Wash. 98607, U.S.A. Department of Electrical and Computer Engineering, University of California at San Diego, 9500 Gilman Drive, MC 0407, La Jolla, Calif. 92093, U.S.A. Japanese Journal of Applied Physics Vol. 44, No. 12, 2005, pp. L 398-L 401"; and is included herein as reference.

The cover 30 further serves to prevent evaporation, and contamination of any contents placed into cavity 32.

Two multiple purpose tubes 26, traverse through the above exterior, and stick out the underside of the cover 30, and slightly (immediately above) into the central cavity 32.

Multiple purpose tubes 26 (FIG. 3) provides means for: introducing cells, as an entry for surgical tools, needles, and water replenishing means, incase water over flows, used as vents, as an entry for a plastic tube releasing dry gases; to name some functions for serving central cavity 32.

The central cavity 32, can be cleaned using a vacuum. Nanowires may be used instead of nanotubes. They can also be used in combination (nanowires/nanotubes). More than 32 nanotubes or nanowires could be added in the final draught.

One example of how to make the housing to FIG. 3:

Both base member 31 and cover 30 are each made in a separate pre fabricated mold. Base member 31 and cover 30 are made of molded plastic resin between 10 and 20 millimeters thick (this is done in two or three steps if need be) and left to set each time between applications of resin. so that the housing will remain solid and provide a first part barrier protection from external electrical currents (stray electrical currents), and magnetic frequencies sources. The support columns 28 each screws into position via the top part of each of the said column 28; into the base member 31 fitted with two holes and tread respectively the same size to match the treaded holes (one hole for each of the 2 columns) in the underside of base member 31 that are revealed once the mold to make base member 31 is removed. Once set all the component described to FIG. 3 that go inside base member 31 and cover 30 are fixed in position along with plastic screws and plastic holders into the base member 31 and cover 30. Then all the said component are tested for any electrical current and magnetic charge problems. Then all is covered (Filled) with diamagnetic silicone (this is the second said barrier protection) and leaving a 7 to 10 millimeter space for a two-part epoxy resin to cover the diamagnetic silicone; and left to set. Then the final said 7 to 10 millimeter space for a two-part epoxy resin is filled and left to set. Both base member 31 and cover 30 can now be removed from there separate molds, and the exterior parts connected, and then tested.

FIG. 4, Shows an above view of the top of base member 31 (FIG. 3) of the housing for controlling very small organism(s); and the central cavity 32 viewed from above, where a cell organism 34, is in direct contact with magnetized water 33. The housing alignment pins 36 in each corner of base member 31. Male connectors 57 east and west of the central cavity 32. Said male connectors 57 are closer to the perimeter of base member 31, to prevent conductive interference with the central cavity 32. When the cover 30 (FIG. 3) is joined with the base member 31 (FIG. 3), as shown and described in FIG. 3. Multiple directional control Is achieved, simultaneously (in every direction), as illustrated in FIG. 4, by: N=North, S=South, W=West, E=East. Internally and externally controlling the cell organism 34, within the central cavity 32.

FIG. 5, shows an above view of the underside of cover 30 (FIG. 3); that is part of the housing for controlling very small organism(s). An interior view of the multipurpose tubes 26 (FIG. 3). Further shows the insertion holes 35, within the multipurpose tubes 26 (FIG. 3). Female connectors 58 east and west of the of the multipurpose tubes 26.

Other Examples of the Present Invention

Yet in another embodiment of the present invention, an image is produced reflecting the changes in polarity of hydrogen molecules. for example using housing of the apparatus to FIG. 1: water found in the base member 18 (FIG. 1) and the water found in living tissues of a human patient 19 (FIG. 1). The image is enabled by rotating the magnetic charge from positive to negative charge that shifts the polarity within hydrogen molecules from north to south, in repeated manner. And is achieved by reversing, then forwarding the polarity of the electromagnets several times a second, (pulsation) causing small radio frequencies waves every time the hydrogen molecules polarity whiten water molecules is shifted accordingly with the electromagnets controlled by the sequencing unit 15 (FIG. 1), and recording the events using computer 12 (FIG. 1) to processes the information received from vibrating hydrogen molecules, into numerical digital image. And then viewing the results on the computer monitor 11 (FIG. 1) Essentially the only limits herein are the preprogrammed sequencing.

The strength of the magnetic field used; is between 0.01 to 1.5 Tesla for a patient where 1 Tesla of MF=42.57 MHz exposure. Although a living cell may require 0.05 Tesla or lower microtesla range MF exposure; since the housing for small organism(s), in FIG. 3, is also enabled to produce an image using the above method. The different being that it utilizes, nonotubes and/or nano wires, instead of electromagnets to precisely reach and equal, such small nano dimensions.

Unlike MRI methods. The present invention records not only the changes of water molecules in a subject. But also the changes in water molecules surrounding the subject.

Since the "hydrophobicity of materials decrease after magnetization", as we learn in the Background of the present invention.

In another embodiment of the present invention. Linking the extractor 17 (FIG. 6) using male tread 46 (FIG. 6) of titanium pipe 45 (FIG. 6) that enters a female treaded plumbing fitting, and in turn connected to a:

Hydroponic housing for treating living vegetation, for horticultural, agricultural, and forestry application(s) to increase the absorption of nutrients; for example: via plant roots; or a shower housing, used for application(s) on living vegetation; for horticultural, agricultural, and forestry application(s).

other applications linking the extractor 17 (FIG. 6) via:

a shower housing having a drain(s), and a pipe(s) that is part of a shower head assembly(s), water temperature control unit comprising: hot/cold water mixer plumbing assembly, thermostatic mixing valve, steam/cold water mixer or a combination thereof; for producing magnetism induced water, water vapor (mist); a shower housing having a drain(s), and a magnetic field induced metal pipe(s) that is part of a shower head assembly(s), water temperature control unit comprising: hot/cold water mixer plumbing assembly, thermostatic mixing valve, steam/cold water mixer or a combination thereof; for producing magnetism induced water, water vapor (mist).

A remote (portable) infrared frequency transmitter/receiver for operating an electric, and/or pneumatic solenoid valve(s) to control flow of a shower head assembly(s) from the exterior for treating a subject that is within reach, of said shower head.

one or more electromagnets placed around said metal pipe, for providing magnetism induced water, water vapor (mist);

a magnetic field producing coil(s) wrapped around said metal pipe, for providing magnetism induced water, water vapor (mist).

What is claimed is:

1. An apparatus for producing a magnetic field and for providing at least one of therapeutic treatments, molecules and molecular ions and ionic compounds to a subject, said apparatus comprising:

a housing for receiving the subject, the housing including a base member and a cover; water contained within a cavity in the base member of said housing;

a plurality of electromagnets, having contact with an equal number of magnets, one on one disposed about the housing for producing a magnetic field in the housing and for magnetizing the water contained within the cavity;

a carbon dioxide ($CO_2$) liquid coolant circulating in and out of the walls of the housing for cooling circuit boards, and the plurality of electromagnets;

a carbon dioxide ($CO_2$) liquid coolant circulating in a cryogenic tube forming a coil around a pipe that generates a catalyst inside said pipe associated with an extractor, wherein the catalyst reaction generates ionic compounds, molecular ions and molecules;

the extractor connected to said housing for transporting the ionic compounds, molecular ions and molecules to the housing;

digital imaging device for tracking the magnetic field as it relates to the water in the housing;

a control sequence unit for controlling an AC/DC power supply and for controlling a solenoid valve associated with the extractor to allow transportation of the ionic compounds, molecular ions and molecules to said housing; and a computer connected to the control sequence unit, the computer including a monitor and a processor, the processor configured to:
control an electric current regulator for providing electric current to circuit boards and to the plurality of electromagnets and the extractor; and
control each circuit boards that control each electromagnet of the plurality of electromagnets independently of others in said plurality of electromagnets, and likewise for each magnet of said plurality of magnets;

wherein said magnetized water is adapted to surround at least a portion of the subject positioned within the housing so as to permit alignment of cells or organisms with and perpendicular to the magnetic field.

2. The apparatus of claim 1, wherein the housing is selected from the group consisting of a shower, sauna, jacuzzi, pool, aquarium, hydroponic container, green house, metal pipe plumbing assembly, water mixer chamber, steam/water mixer, bag, and vial.

3. The apparatus of claim 1, wherein each of the electromagnets comprises a para-magnetic core and, a coil, wherein a magnetic field is produced in an axial cylindrical bore of the coil.

4. The apparatus of claim 3, wherein the plurality of electromagnets are disposed within a wall of the base member, and cover of the housing.

5. The apparatus of claim 4, further comprising a diamagnetic material disposed between each of the plurality of electromagnets.

6. The apparatus of claim 1, wherein the cavity is formed in a center of a top surface of the base member and is bowl shaped.

7. The apparatus of claim 1, wherein the plurality of electromagnets are nanotubes or nanowires.

8. The apparatus of claim 7, wherein the plurality of electromagnets are nanotubes, and the plurality of nanotubes are contained in the base member and the cover.

9. The apparatus of claim 7, wherein the plurality of electromagnets for said base member and said cover comprises each between 4 and 32 nanotubes.

10. The apparatus of claim 8, wherein the nanotubes are sandwiched in diamagnetic material.

11. The apparatus of claim 1, wherein the cover is disposed on top the base member, a plurality of pins are disposed along a perimeter of an underside of said cover, a plurality of holes are formed along a perimeter in a top surface of the base member, wherein the plurality of pins engage the plurality of holes in order to align the cover with the base member.

12. The apparatus of claim 1, wherein the extractor comprises a cover with a housing containing a drug(s) or compound(s) and a superconductive wire forming a loop inside the housing.

* * * * *